United States Patent [19]
Demane et al.

[11] Patent Number: 4,995,883
[45] Date of Patent: Feb. 26, 1991

[54] MODULAR HIP PROSTHESIS

[75] Inventors: Michael Demane; Thomas W. Fallin; Steve Garner, all of Memphis; Jeff Schryver, Cordova, all of Tenn.

[73] Assignee: Smith & Nephew Richards Inc., Memphis, Tenn.

[21] Appl. No.: 308,205

[22] Filed: Feb. 8, 1989

[51] Int. Cl.$^5$ ............................ A61F 2/34; A61F 2/30
[52] U.S. Cl. .......................................... 623/23; 623/18
[58] Field of Search ........................ 623/16, 18, 19, 20, 623/21, 22, 23

[56] References Cited

U.S. PATENT DOCUMENTS

| | | | |
|---|---|---|---|
| 4,187,559 | 2/1980 | Grell et al. | 623/18 |
| 4,670,015 | 6/1987 | Freeman | 623/23 |
| 4,693,724 | 9/1987 | Rhenter et al. | 623/23 |
| 4,698,063 | 10/1987 | Link et al. | 623/23 |
| 4,840,632 | 6/1989 | Kampner | 623/23 |
| 4,842,606 | 6/1989 | Kranz et al. | 623/23 |

FOREIGN PATENT DOCUMENTS

| | | | |
|---|---|---|---|
| 0295360 | 12/1928 | European Pat. Off. | 623/23 |
| 0257359 | 3/1988 | European Pat. Off. | 623/23 |
| 0290735 | 11/1988 | European Pat. Off. | 623/23 |
| 2524923 | 11/1976 | Fed. Rep. of Germany | 623/23 |
| 2724041 | 11/1978 | Fed. Rep. of Germany | 623/18 |
| 3336005 | 4/1985 | Fed. Rep. of Germany | 623/18 |

*Primary Examiner*—David J. Isabella
*Attorney, Agent, or Firm*—Pravel, Gambrell, Hewitt, Kimball & Krieger

[57] ABSTRACT

A modular hip prosthesis can be custom fitted to a particular patient by a surgeon prior to surgical insertion. The prosthesis features a body having a neck portion for carrying a rounded head element, a transitional mid-section of the prosthesis body includes generally rectangular and generally rounded cross-sectional areas, and a stem section has a generally rounded cross-sectional area. The stem is tapered to receive a tubular extension sleeve with a hollowed portion corresponding in shape to the stem portion of the prosthesis. The tubular extension sleeve has an open end portion receptive of the lower tapering stem of the prosthesis body. The stem portion including an internal bore, and an attachment in the form of an elongated screw is provided for connection to the stem internal bore for securing the extension sleeve and the prosthesis body together, forming a compressive sealed connection therebetween. Pads can be attached to the transitional mid-section of the prosthesis body for increasing the cross-sectional shape of the prosthesis at the transitional mid-section. Removable collars can be added to the prosthesis to form a transverse load carrying interface with the upper end of the patient's femur. Frustro-conically shaped extension sleeves can be added to the prosthesis neck for extending the neck length.

15 Claims, 4 Drawing Sheets

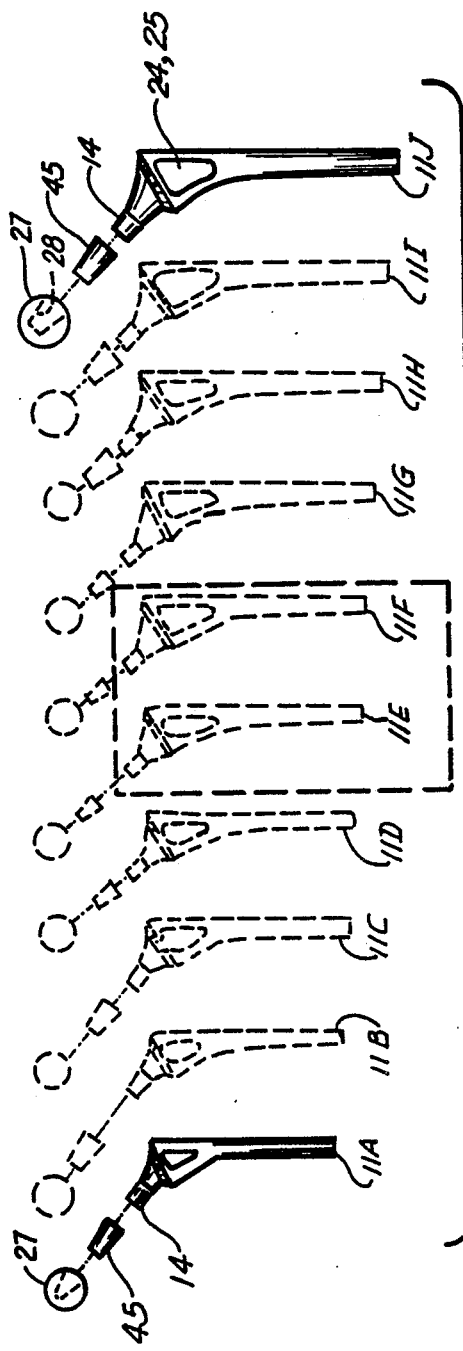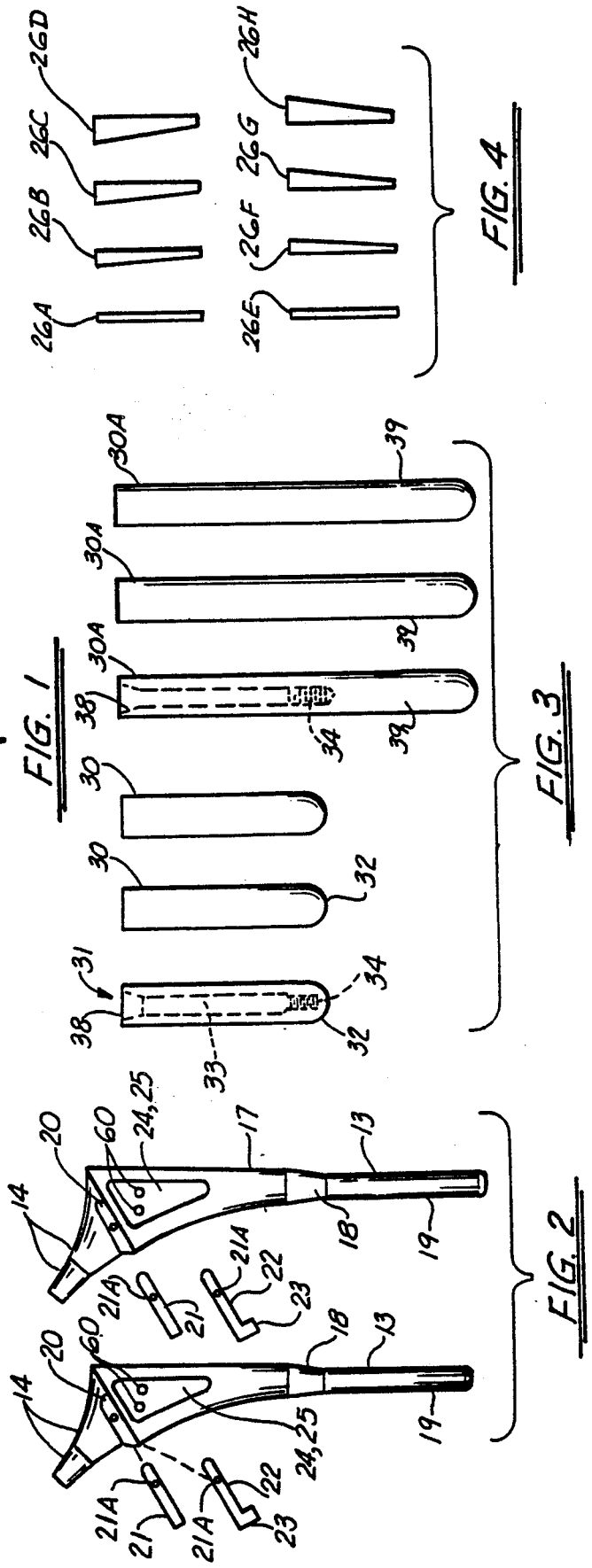

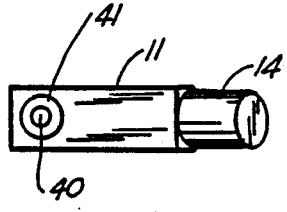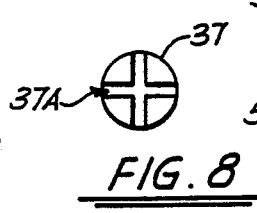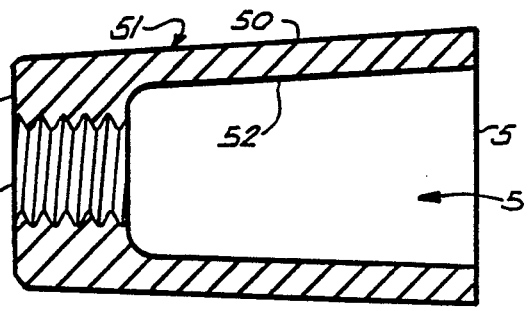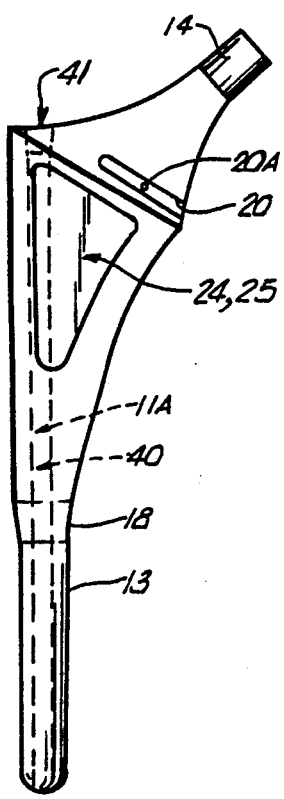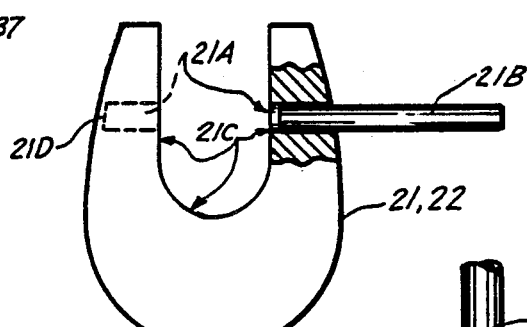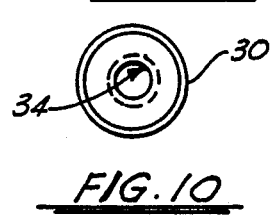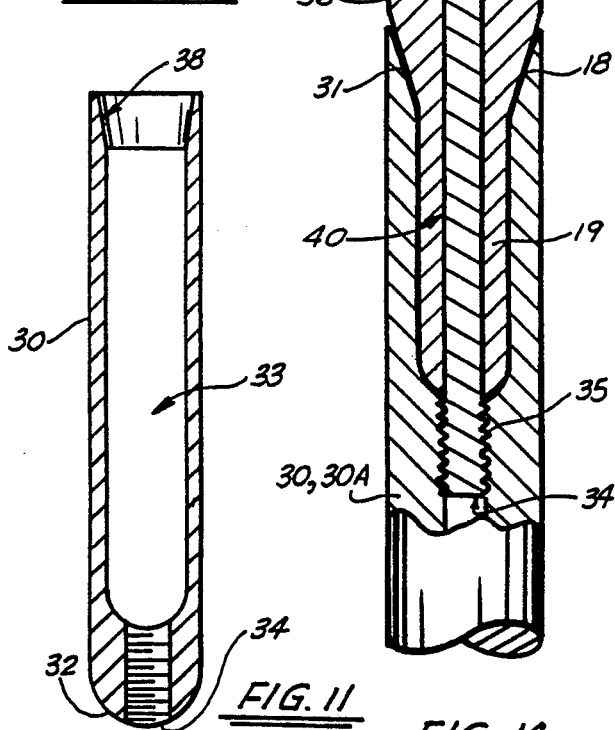

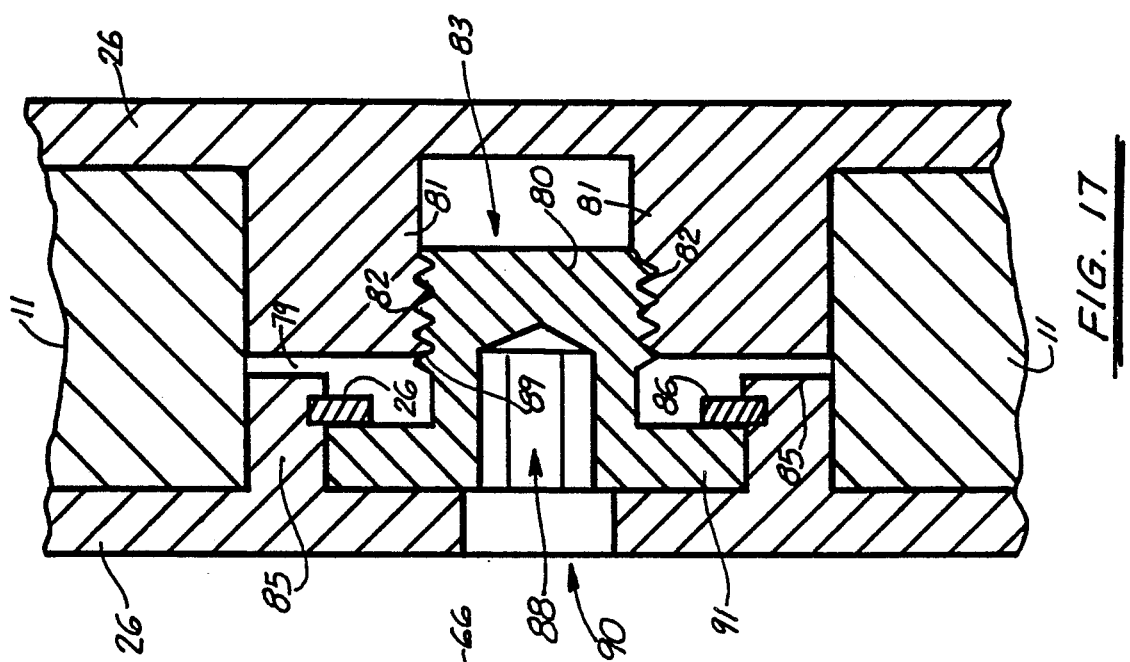
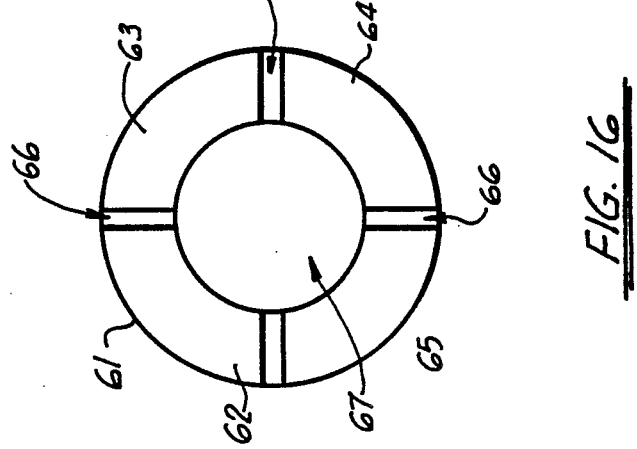
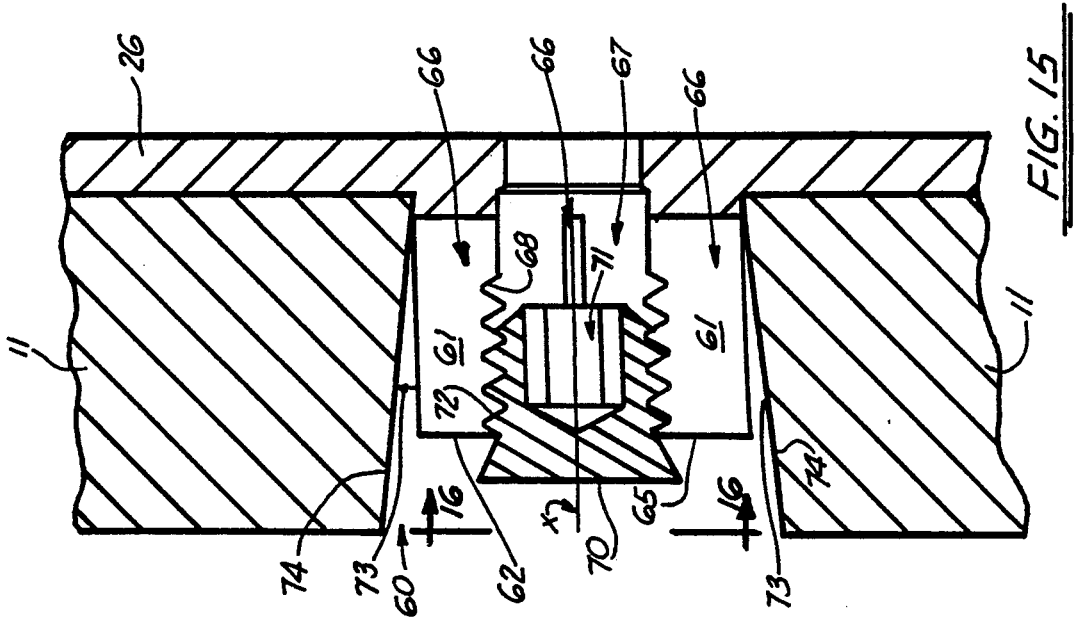

4,995,883

MODULAR HIP PROSTHESIS

BACKGROUND OF THE INVENTION

1. Field of the Invention

The present invention relates to a modular hip prosthesis system wherein various component parts of an implant can be selected during the surgical procedure so that the implant can be custom fitted to a patient.

2. General Background

Increasingly, surgeons want to be able to custom fit femoral prostheses to patients. Instead of having to choose a properly sized prosthesis from a group of pre-formed implants, it would be advantageous to have a basic design which can be modified with various component parts. This would eliminate the need to maintain a large inventory and would provide better fitting implants.

Custom fitted implants are particularly important in revision cases where an implant has to be removed and replaced since old cement must be removed and bone resorption occurs in many cases. Unpredictable, proximal and/or distal bone loss or deformity often occurs which must be accommodated by the replacement prosthesis.

For initial implants, basic variations in patient anatomy are often confronted by the surgeon. Some patients have femoral necks that can be significantly longer or shorter than others. Cortical shaft defects, which are not uncommon, are not discovered until during operation. Variations in intramedullary canal diameter can also occur, which if not accompanied by a properly sized implant, can result in distal toggle.

In short, it is difficult, if not impossible, to predict the exact shape of a hip implant which is suitable for all patients. Since it is impractical and would be prohibitively expensive to maintain an inventory of implants for most patients, compromises must sometimes be made in supplying implants which fit reasonably well but could be improved upon.

Several hip prostheses are known which are formed of replaceable or interchangeable component parts.

U.S. Pat. No. 3,641,590 entitled "Acetabular Replacement Prosthesis and Method of Assembling" issued to Michele discloses a selective individualized technique for acetabulum socket replacement per se, or in conjunction with a hip replacement prosthesis (referring to the Michele U.S. Pat. No. 3,228,393) for a total hip replacement, designed for all ages including the very young. A selective anchorage for a cup prosthesis of a size selected from the limited number of differently sized cups is made available. Anchorage of the acetabular socket replacement conforms to variations in dimensions, shapes and positions of the (medullary) canals of the acetabulum pelvis of the individual patient and includes at least two elongated and convergent or divergent fasteners.

A removable collar of low modulus of elasticity material is shown in U.S. Pat. No. 4,012,796 entitled "Interpositioning Collar For Prosthetic Bone Insert" issued to Weisman et al. The collar is interpositioned between a collar of a metal prosthetic hip stem implanted in the intramedullary canal of the femur and the adjacent calcar or outer edge of the bone. A flange depends from the insert between the upper portion of the stem and the inner wall of the bone. The interpositioned collar is either a full elongated tapered 0-shape or it is open on one side of a tapered U-shape.

U.S. Pat. No. 4,404,691 entitled "Modular Prosthesis Assembly" issued to Buning et al., provides a modular hip prosthesis assembly for replacement of at least part of a joint and part of a bone shaft including a mounting component provided with a connection portion and at least two joint components of similar shape but different dimensions and which can be connected alternatively to the mounting component, each of the joint components having an engagement portion and a connection part adapted for connection to the connection portion of the mounting component, the joint components each providing part of a bone shaft and part of a joint which can cooperate with an appropriate part of a natural or artificial joint.

U.S. Pat. No. 4,578,081 entitled "Bone Prosthesis" issued to Harder et al., discloses a bone prosthesis comprising at least one joint component replacing a natural joint half, which is provided with a shank adapted to be connected to the bone, wherein a set of joint components is provided, and the shank is designed as a bone replacement member, with a connection portion provided adapted to be connected to the bone at one end and at the other end to the shank. One of the components is a hip prosthesis with a rounded head and a hollowed hip component that connects to elongated mounting components. In another hip prosthesis embodiment, a neck with a cone shape receives a suitable joint head with an inner cone.

A femoral component for hip prosthesis is shown in U.S. Pat. No. 4,608,055 issued to Morrey et al., the prosthesis disclosed in the '055 patent includes a stem portion and a combined integral head and neck portion. The stem portion includes a proximal portion and a distal portion which are angularly related with respect to one another and with the proximal portion including a recess formed therein for receipt of the tapered portion of the head and neck component. The head and neck component includes a substantially part spherical head portion attached to a neck portion and a tapered portion angularly attached to the neck portion via a basalar neck portion with the tapered portion being adapted to be permanently inserted into the recess portion of the proximal end of the above described stem portion. The stem portion includes a plurality of recesses on the periphery and longitudinal extent thereof for receiving fiber metal pads which are provided to allow boney ingrowth therein in order to retain the femoral component permanently installed in the proximal end of the femur.

In U.S. Pat. No. 4,676,797 entitled "Unit For Resection Prosthesis", a resection prosthesis assembly unit includes a head member, an end member and an intermediate member between the head and end members, of which one member is provided with a conical pin and another member is provided with a conical pin and another member is provided with a conical bore. The latter two members are provided with respective first surfaces extends transversely to an insertion direction and which face one another and are spaced apart to define a recess when the two members are connected together. One of the two members is further provided with a second surface extending in the insertion direction, and the recess being provided to receive a wedge insertable into the recess to bear against the first surfaces for forcing the two members apart while the forces exerted by the wedge are absorbed by the first surfaces and the wedge is guided by the second surface.

Stem extensions and/or augmentation are provided which allows the length of the femoral shaft to be augmented with extensions that lock with the primary shaft using a tapered attachment. This attachment allows the surgeon to extend the stem length beyond any cortical shaft defect he may encounter intraoperatively. Additionally, end fitting caps attached in a similar fashion could allow the surgeon to tailor the prosthesis tip to the canal diameter thereby reducing distal toggle. The prosthesis bodies could be provided in a variety of inclinations of the access of the modular head and or neck module with respect to the longitudinal axis of the prosthesis body and the stem. The surgeon could intraoperatively select the most appropriate amount of version (anteversion or retroversion) to restore joint stability. Increase attainable neck length variation is provided for allowing "fitting" to patients with very short femoral neck (i.e. CDH, small females) or very long femoral necks (i.e. to components for proximal bone loss). Head neck assemblies could also incorporate a collar or augmented extension to convert the standard stem body into a proximal ⅓ replacement or a revision stem. A separate set of head neck assemblies could be offered to allow the surgeon to tailor the neck shaft angle of the assembled device as well.

SUMMARY OF THE PRESENT INVENTION

The present invention provides a modular hip prosthesis which can be custom fitted to a particular patient by a surgeon prior to surgical insertion of the prosthesis.

The apparatus includes a prosthesis body having a wider upper mid-section portion and an upper neck adapted for carrying a rounded head portion that fits either the patient's acetabulum or a prosthetic acetabular component. A lower stem extends from the mid-section and terminates at a lower rounded tip. The stem is adapted for placement in the intramedullary canal of the patient's femur.

A tubular stem extension sleeve includes a hollowed portion corresponding in shape to the stem. The extension sleeve includes an open end portion which is receptive of the stem for insertion thereinto. The lower stem portion includes an internal bore. An attachment member, preferably in the form of a threaded draw bolt, forms an attachment between the internal bore of the stem and the extension sleeve holding the extension sleeve to the prosthesis body.

The stem and sleeve form a tight friction fit which seals wear particles from body tissues that typically wear off during insertion of the stem to the sleeve. When the draw bolt is tightened, its non-threaded end presses against the hip stem to provide tension in the bolt and compressive force between the stem and sleeve in corresponding tapered regions of the stem and sleeve. The corresponding tapered regions thus register tightly together forming a seal.

The tubular stem extension sleeve is of a generally uniform cross-section. Its upper end has an annular tapered section that registers with correspondingly tapered section of the stem. The prosthesis body in one embodiment has a longitudinal central open ended bore that extends substantially the length of the prosthesis body. The attachment includes an elongated fastener, preferably an elongated threaded bolt that is adapted for placement within the elongated bore, extending substantially the length of the bore upon assembly. The bolt provides an upper head end portion which can be manipulated by the surgeon at the top of the prosthesis for tightening or loosening the fit between the sleeve and prosthesis body. The stem extension sleeve provides a threaded section that can engage the lower end portion of the bolt to form a threaded connection. This attachment of sleeve and prosthesis body can also be made using a very short bolt which is affixed through an opening in the bottom of the extension sleeve, and into a bore in the bottom of the stem.

The prosthesis body has a frustro-conically shaped neck portion for carrying a rounded head element. Between the neck portion and the stem is a transitional mid-section having generally rectangular upper and a generally rounded lower cross-sectional area. Extension sleeves can be added to the neck portion for elongating the neck portion with respect to the prosthesis body and the head.

Removable transverse bearing collars can be adjustably affixed to the mid-section of the prosthesis body, generally transverse to the longitudinal axis of the prosthesis body for forming a load carrying interface between the prosthesis body and the upper end of the patient's femur. In one embodiment, the removable bearing collar can have extensions that will compensate for proximal bone loss, i.e. at the top of the patient's femur.

Removable pads are attachable to the transitional mid-section of the prosthesis for increasing the cross-sectional area of the prosthesis at the transitional mid-section. One or more transverse openings formed in the prosthesis at the transitional mid-section carry attachments for securing the pad to the prosthesis. The pads carry corresponding interlocking members which attach through the transverse opening of the prosthesis body forming a connection with each other, holding the pads to the prosthesis body. Pad shape can be varied to custom fit the patient's anatomy maximizing stability to transfer shear load or compression load between the prosthesis and the patient's bone as desired. The pads can be of differing materials such as porous or roughened coatings to promote tissue ingrowth or on growth. Also, manufacturing methods which might weaken the integrity of the prosthesis body, such as the addition of a coating of beads, can be used for the removable pads, thus not affecting the structural integrity of the prosthesis body.

The stem extension sleeve can be of varying lengths and be straight or curved and the bore portion thereof can be substantially the length of the extension sleeve or extend a partial distance along the extension sleeve so that the extension sleeve can extend beyond the point of attachment of the stem to the extension sleeve at the lower end portion of the stem.

The assembly draw bolt can be tightened after the prosthesis and extension sleeve are in position so that the extension can twist to track the intermedullary canal during insertion. After placement, the draw bolt locks the extension and prosthesis body together.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is a side view illustrating a plurality of hip prosthesis bodies as used with the modular hip system of the present invention;

FIG. 2 is a side view of a pair of hip prosthesis bodies of differing sizes illustrating insertion of the modular collar portions thereof;

FIG. 3 is a side view illustrating a plurality of sleeve extension parts as used in the modular hip prosthesis system of the present invention;

FIG. 4 is a side view of a plurality of modular pads for use with the hip prosthesis bodies of FIGS. 1 and 2, illustrating varying pad cross-sectional configurations;

FIG. 6 is a top view of the prosthesis body portion of the preferred embodiment of the apparatus of the present invention;

FIG. 7 is a side view of the prosthesis body portion of the preferred embodiment of the apparatus of the present invention;

FIGS. 8 and 9 are top and side views illustrating the assembly bolt portion of the preferred embodiment of the apparatus of the present invention;

FIGS. 10 and 11 are top and side sectional views of the stem extension sleeve portions of the preferred embodiment of the apparatus of the present invention;

FIG. 12 is a sectional view illustrating an alternate construction of the neck extension sleeve portion of the preferred embodiment of the apparatus of the present invention;

FIG. 13 is a plan view illustrating the modular collar portion of the preferred embodiment of the apparatus of the present invention;

FIG. 14 is a partial sectional view illustrating the preferred embodiment of the apparatus of the present invention with the prosthesis body and stem extension sleeve assembled;

FIG. 15 is a sectional elevational fragmentary view illustrating the assembly of modular pads to the prosthesis body;

FIG. 16 is a sectional view taken along 16—16 of FIG. 15; and

FIG. 17 is a sectional elevational view of another embodiment illustrating the assembly of modular pads to the prosthesis body.

DETAILED DESCRIPTION OF THE PREFERRED EMBODIMENT

Figure 5:
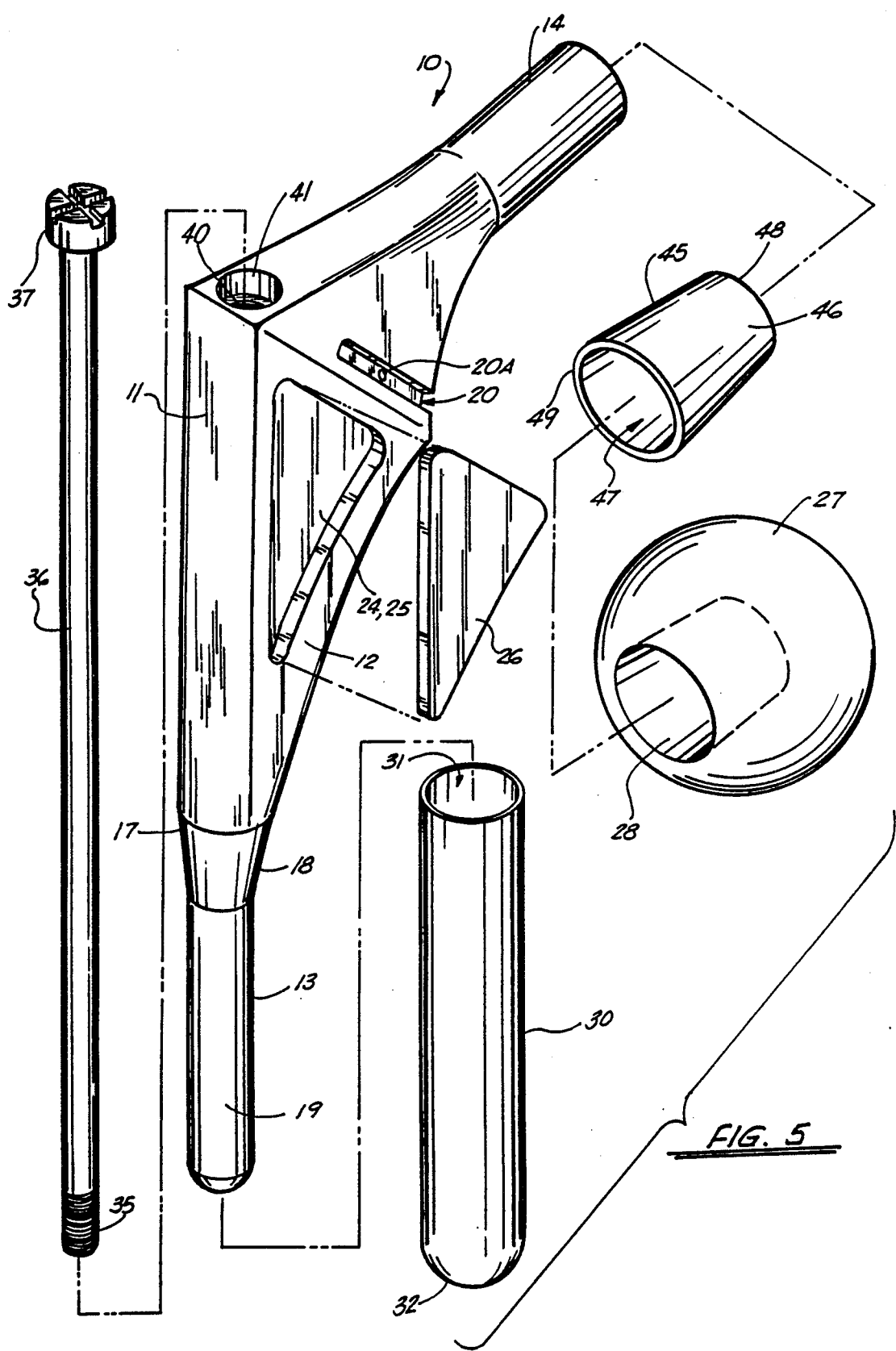
FIG. 5 is a perspective exploded view illustrating the preferred embodiment of the apparatus of the present invention.

FIGS. 1-5 illustrate generally the preferred embodiment of the apparatus of the present invention designated generally by the numeral 10. In FIG. 5 there can be seen a prosthesis body 11 which includes a widened mid-section 12, a lower elongated generally cylindrically shaped stem 13 and an upper neck 14. The mid-section includes an upper generally rectangular cross-sectional portion 15 and a lower generally rounded cross-sectional portion 16 which communicates with the generally cylindrical stem 13.

The stem 13 includes three sections including an upper cylindrical section 17, a frustro-conical tapered transition section 18 and a lowermost smaller-diameter cylindrical portion 19. The prosthesis body 11 would preferably be supplied to hospitals and surgeons in kit form with a plurality of prosthesis bodies 11, pads 26, heads 27, collars 21, 22 and extension sleeves 30 being offered in various sizes such as is shown in FIGS. 1-2, including prosthesis bodies 11A-11J. Each prosthesis body 11 includes a generally U-shaped annular recess 20 which extends around one edge of the transitional mid-section 12 portion of the body 11 and is receptive of generally U-shaped collars 21 or 22 (FIG. 2). Recess 20 has a shape corresponding to the inner edge portion 21C of collar 21. Collar 21 is thus generally U-shaped in plan view (FIG. 13). Another embodiment of U-shaped collar 22 provides a similar, generally U-shaped body in plan view, but also includes a downwardly extending tab 23 which can be used to help transfer load between the prosthesis 10 and the femur where proximal bone tissue has eroded. Lock pin 21B (FIG. 13) extends through openings 21A, 20A in order to secure collars 21, 22 to prosthesis body 11. One of the openings 21A can be formed as a blind hole with a wall 21D and not extend all the way to the outer surface of the collar so that the pin 21B cannot be driven too far and project from the outer surface of the collar 31.

Each prosthesis body 11 includes a pair of left and right sockets 24, 25 which are receptive of one or more adjustment pads 26A-26H. Notice that the cross-sectional configuration of each pad 26A-26H can vary including thicker portions of the pad at the top as compared with the thickness at the bottom such as for example can be seen in FIG. 4 with pad 26D and pad 26H which are thicker at one edge as compared with pads 26A and 26E. The pads 26A-26H can be added by the surgeon to give a custom fit to the prosthesis body 11 in the area of the mid-section 12.

Neck 14 is a frustro-conically shaped neck receptive of head 27. Head 27 provides a socket 28 corresponding in shape to neck 14. A plurality of heads 27 can be provided in various sizes as part of the kit, for matching each respective prosthesis body 11A-11J.

Stem 13 is rounded at its lower tip. The lowermost portion 19 of stem 13, which is of a smaller diameter, and the frustro-conical transition portion 18 of stem 13 form an attachment with a stem extension sleeve 30 (FIGS. 3, 5, 10, 11, and 14). The sleeve 30 is elongated and generally cylindrical and has an open end 31 which allows insertion of the stem 13 thereinto. The lowermost end portion of the sleeve 30 includes a generally curved distal end portion 32. Extension sleeve 30 is hollow providing a longitudinally extending bore 33 which extends between open end 31 and threaded aperature 34. Aperature 34 extends downwardly from bore 33, communicating with end 32. Threaded aperature 34 is receptive of the external threads 35 of a draw bolt 36. Bolt 36 includes an uppermost head portion 37 and a lower threaded portion 35. Prosthesis body 11 thus includes a longitudinally extending central bore 40 that is receptive of elongated bolt 36. The upper end portion of extension sleeves 30, 30A includes a bevelled inner annular surface 38 (FIGS. 3 and 11) which corresponds in shape to the frustro-conical transition portion 18 of stem 13 so that extension sleeves 30, 30A and stem 13 can form a frictional tight fit upon assembly (see FIG. 14). Draw bolt 36 would be tightened after placement of prosthesis body 11 and a sleeve 30 or 30A into the intramedullary canal. Thus the extension sleeve 30 or 30A is free to track the natural path of the intramedullary canal during insertion. After insertion bolt 40 is tightened, drawing annular bevelled surface 38 of sleeve 30 or 30A 30A and transition portion 18 of stem 13 together.

Extension sleeve 30 can be a short version having a longitudinally extending bore 3 which communicates with aperature 34, extending to end 32. In another embodiment (see FIG. 3), extension sleeve 30A can be elongated extending well beyond threaded aperature 34. As shown in the longer sleeve in FIG. 3, the longitudinal axis of extension sleeve 30A can change angle slightly or have a curvature in order to track the intramedullary canal, with the lower end portion 39 of each extension sleeve 30A being solid and being slightly skewed with respect to the longitudinal axis of open bore 33. This allows the extension sleeve 30A to track the natural path of the intramedullary canal which is not perfectly straight nor a pure elongated cylinder. Thus, the elongated extension sleeves 30A can conform naturally to the femur of a patient for a custom fit.

A plurality of heads 27 of differing sizes would be provided. The distance between the prosthesis body and the head 27 could be varied using extension members 45 or 50. Extension member 45 would be a hollowed trunion having a conical outer surface 46 and a corresponding conical inner surface 47. A smaller open end portion 48 and a larger open end portion 49 define therebetween a bore which is occupied by neck 14 upon assembly of extension member 45 thereupon. Because of the smaller end 48, a head 27 could simply be slipped upon the extension member 45 with the socket 28 of head 27 registering upon the outer surface 46 of the extension member 45. In the preferred embodiment, extension members 45 of differing lengths and of different cross-sectional dimensions would be provided to correspond to the plurality of differing neck sizes that accompany the plurality of prosthesis bodies as provided in kit form (see FIG. 1).

An alternative trunion construction is shown in FIG. 12 wherein the extension member 50 includes a conical outer surface 51, a conical inner surface 52 with a small end portion 53 having a threaded opening 54 that communicates with socket 56 at large diameter end portion 55 of extension member 50. Thus, the socket 28 of a particular selected head 27 would be registered upon the end of extension member 50. In order to remove the member 50 from neck 14, the threaded opening 54 would be threadably engaged with a removal tool in the form of a shaft having one end portion which is threaded and the opposite end portion defining a handle, for example.

In FIGS. 15-17, pads 26 are shown as removably attached to prosthesis body 11. In FIG. 15, it should be understood that only the assembly for securing one pad 24 or 25 is shown.

In the embodiment of FIG. 17, the pads 26 are held in place by a single attachment mechanism that is carried generally between the pads 26 forming a connection therebetween.

In the embodiment of FIG. 15 there is provided an annular bushing 61 which is an extension of each pad 26. Bushing 61 includes a plurality of arcuate members 62-65 with spaces 66 therebetween so that the bushing 61 can expand and grip the beveled annular wall 74 of opening 60 in prosthesis body 11 which is doubled. A bolt 70 is threadably attached to threaded bushing 61 so that the threads 72 of bolt 70 register with and threadably engage the threads 68 of bushing 61. Upon such threadable connection, the individual arcuate members 62-65 of bushing 61 expand (see arrows 73 of FIG. 15) bearing against the annular wall 74 of opening 60. An opening 67 in pad 26 communicates with a tooled opening 71 in bolt 70 so that a tool such as an allen wrench for example can be inserted through opening 67 and into registration with the slot 71 which would be correspondingly shaped to the tool used.

In the embodiment of FIG. 17, a single assembly bolt 80 is used to secure a pair of pads 26 together upon prosthesis body 11. The prosthesis body 11 includes a cylindrical transverse opening 79 which is occupied by annular bushing 81 integrally attached to pad 26. Bushing 81 includes an inner socket portion 83 which is threaded with internal threads 82. Assembly bolt 80 provides corresponding external threads 89 which threadably engage the threads 82 of bushing 81. A socket 88 is receptive of a tool such as an allen wrench for example and rotates therewith to tighten pads 26 together. Pad 26 provides a bushing 85 which carries an annular retaining ring 86, which can be a split ring or the like. An opening 90 allows access through pad 26 to the tooled opening 88. Assembly bolt 80 includes a generally circular annular head portion 91 which is held against pad 25 with ring 86. As the threaded bolt 80 is tightened, pads 26 are thus pulled together and tightly against prosthesis body 11.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An implantable modular hip prosthesis that can be custom fitted to a particular patient by a surgeon prior to surgical insertion, comprising:
   (a) a hip prosthesis main body having an upper proximal end portion and a lower stem portion, said proximal upper end portion including a neck portion extending from the main border and adapted to be coupled to a rounded joint head portion that is configured to engage the acetabulum;
   (b) the lower stem portion extending distally from the main body and terminating at a rounded tip and having an internal through bore formed therein along the length thereof;
   (c) an elongated tubular sleeve terminating at opposite ends and at least a portion of the sleeve being hollowed and opening at one end thereof wherein the hollowed portion is configured in shape for receipt of the stem lower end portion receptive of the stem;
   (d) an elongated connecting rod having attachment means at one end thereof for operatively coupling the sleeve to the main body wherein the tubular sleeve is disposed over the lower stem portion and the connecting rod is inserted into the through bore and the attachment means is coupled to the tubular sleeve thereby forming a modular prosthesis that can be custom fitted to a particular patient prior to surgical insertion by interchanging sizes of the various components.

2. The modular hip prosthesis of claim 1 wherein the tubular sleeve is of a generally uniform cross-section.

3. The modular hip prosthesis of claim 1, wherein the tubular sleeve is substantially straight.

4. The modular hip prosthesis of claim 1 wherein the prosthesis main body comprises an uppermost neck block portion having a neck for carrying the rounded joint head portion, a transitional mid-section portion extending downwardly from the neck block portion and including an uppermost generally rectangular horizontal cross-sectional portion and a lowermost generally rounded cross-sectional areas and a stem section having a generally rounded cross-sectional portion, and the stem section has a generally rounded horizontal cross-sectional area that communicates with the rounded cross-sectional portion of the neck block portion.

5. The modular hip prosthesis of claim 1 wherein the sleeve has a bore that extends substantially the length of the sleeve.

6. The modular hip prosthesis of claim 1 wherein the sleeve has a bore that extends partially the length of the sleeve.

7. The modular hip prosthesis of claim 4 wherein the neck has a frusto-conically shaped outer surface.

8. An implantable modular hip prosthesis that can be custom fitted to a particular patient by a surgeon prior to surgical insertion, comprising:
   (a) a hip prosthesis main body having a proximal upper end portion and a lower stem portion, a neck member extending from the main body and adapted to be coupled to a rounded joint head that is configured to engage the acetabulum;
   (b) said lower stem portion extending distally from the main body and terminating at the rounded tip and adapted for placement in the intramedullary canal of the patient's femur;
   (c) an elongated tubular sleeve terminating at opposite ends and having at least a portion of the sleeve hollowed and opening at one end portion thereof wherein the hollowed portion is configured for receipt of the lower stem portion;
   (d) an elongated connecting rod having attachment means at one end thereof for operatively coupling the sleeve to the main body; and
   (e) wherein the tubular stem extension sleeve is disposed over the lower stem portion and the connecting rod is inserted into the through bore and the attachment means is coupled to the tubular sleeve thereby forming a modular prosthesis that can be custom fitted to a particular patient prior to surgical insertion by interchanging sizes of the various components, and the sleeve is curved to conform to the shape of the intermedullary canal.

9. An implantable modular hip prosthesis, comprising:
   (a) a hip prosthesis main body having a proximal upper end portion and a lower stem portion, said proximal upper end portion including a neck member extending from the main body and adapted to be coupled to a joint head portion that is configured to engage the acetabulum portion of the joint, said lower stem portion extending distally from the main body and terminating at the rounded tip, and being adapted for placement in the intramedullary canal of the patient's femur;
   (b) an elongated tubular sleeve terminating at opposite ends and having a hollowed portion configured for receipt of the lower stem portion;
   (c) an elongated connecting rod having attachment means for securing the extension sleeve and prosthesis body together; and
   (e) attachable bearing collar means affixable to the main body generally transverse to the longitudinal axis of the prosthesis main body for forming a load carrying interface with the upper end of the patient' femur.

10. An implantable modular hip prosthesis, comprising:
   (a) a hip prosthesis main body having a proximal upper end portion and a lower stem portion, said proximal upper end portion including a neck member extending from the main body and adapted to be coupled to a joint head portion that is configured to engage the acetabulum portion of the joint, said lower stem portion extending distally from the main body and terminating a rounded tip, and being adapted for placement in the intramedullary canal of the patient's femur;
   (b) an elongated tubular sleeve terminating at opposite ends and having a hollowed portion configured for receipt of the lower stem portion;
   (c) attachment means for securing the extension sleeve and prosthesis main body together, forming a seal therebetween;
   (d) the prosthesis main body including a rounded neck block portion adapted for carrying a rounded joint head element; and
   (e) the main body having anterior and posterior sockets thereon that are positioned generally below the rounded neck block portion and generally above the stem, and removable pad means attachable to the main body at the sockets for increasing the cross-sectional area of the prosthesis main body.

11. The modular hip prosthesis of claim 10 further comprising a transverse opening in the prosthesis main body, and means carried by the pad means, and extending into the transverse opening, for holding the pad means to the prosthesis body.

12. The modular hip prosthesis of claim 11 wherein the pad means comprises a pair of pad members, each carrying the holding means.

13. The modular hip prosthesis of claim 12 wherein the holding means includes in part a locking member on the rear surface of each pad that fits generally between the pair of pads upon assembly of the pads to the main body.

14. An implantable modular hip prosthesis, comprising:
   (a) a hip prosthesis main body having a proximal upper end portion and a lower stem portion, said proximal upper end portion including a neck member extending from the main body and adapted to be coupled to a joint head portion that is configured to engage the acetabulum portion of the joint, said lower stem portion extending distally from the main body and terminating at the rounded tip, and being adapted for placement in the intramedullary canal of the patient's femur;
   (b) an elongated tubular sleeve terminating at opposite ends and having a hollowed portion configured for receipt of the lower stem portion;
   (c) an elongated connecting rod having attachment means for securing the extension sleeve and prosthesis body together;
   (d) the prosthesis main body including a rounded neck block portion adapted for carrying a rounded head element, a transitional mid-section portion and a stem section having a generally rounded cross-sectional area;
   (e) a neck having a frustro-conically shaped outer surface;
   (f) a frusto-conically shaped neck extension sleeve registering upon the neck for extending the neck length.

15. The modular hip prosthesis of claim 14 wherein the extension sleeve is an annular member having corresponding inner and outer shaped surfaces.

* * * * *